US011045111B1

(12) United States Patent
Reddy

(10) Patent No.: US 11,045,111 B1
(45) Date of Patent: Jun. 29, 2021

(54) REAL TIME BREATH ANALYZER FOR DETECTING VOLATILE ORGANIC COMPOUNDS AND IDENTIFYING DISEASES OR DISORDERS

(71) Applicant: Canary Health Technologies Inc., Cleveland, OH (US)

(72) Inventor: Raj Reddy, Burlington (CA)

(73) Assignee: Canary Health Technologies Inc., Cleveland, OH (US)

(*) Notice: Subject to any disclaimer, the term of this patent is extended or adjusted under 35 U.S.C. 154(b) by 0 days.

(21) Appl. No.: 16/877,473

(22) Filed: May 18, 2020

(51) Int. Cl.
| | |
|---|---|
| *A61B 5/08* | (2006.01) |
| *A61B 5/097* | (2006.01) |
| *A61B 5/083* | (2006.01) |
| *G01N 33/497* | (2006.01) |
| *G01N 27/12* | (2006.01) |

(52) U.S. Cl.
CPC ............ *A61B 5/082* (2013.01); *A61B 5/097* (2013.01); *G01N 27/127* (2013.01); *G01N 33/497* (2013.01); *A61B 5/083* (2013.01); *G01N 2033/4977* (2013.01)

(58) Field of Classification Search
CPC ............ G01N 27/127; G01N 33/497; G01N 2033/4977; G01N 2033/4975; A61B 5/082; A61B 5/097; A61B 5/083; A61B 5/08; A61B 5/087; A61B 5/00; A61B 5/6898; A61B 5/7267; A61B 5/1118; G16H 40/67
USPC .................................................. 600/529–543
See application file for complete search history.

(56) References Cited

U.S. PATENT DOCUMENTS

| | | | | |
|---|---|---|---|---|
| 6,234,006 | B1* | 5/2001 | Sunshine | G01N 33/0009 73/29.01 |
| 6,244,096 | B1* | 6/2001 | Lewis | A61B 5/00 422/78 |
| 6,467,333 | B2* | 10/2002 | Lewis | A61B 5/00 422/84 |
| 6,981,947 | B2* | 1/2006 | Melker | A61B 5/08 600/532 |
| 7,052,468 | B2* | 5/2006 | Melker | G01N 29/022 600/529 |
| 7,104,963 | B2* | 9/2006 | Melker | A61B 5/0836 128/203.12 |
| 7,153,272 | B2* | 12/2006 | Talton | A61B 5/097 600/543 |
| 7,820,108 | B2* | 10/2010 | Lampotang | A61B 5/4833 422/84 |
| 2002/0017125 | A1* | 2/2002 | Lewis | A61B 5/082 73/31.05 |
| 2002/0177232 | A1* | 11/2002 | Melker | G01N 29/069 436/151 |

(Continued)

OTHER PUBLICATIONS

Mahari, et al., "eCovSens-Ultrasensitive Novel In-House Built Printed Circuit Board Based Electrochemical Device for Rapid Detection of nCovid-19" bioRxiv, Apr. 24, 2020, 059205, Posted May 11, 2020, pp. 1-20 (Year: 2020).

(Continued)

*Primary Examiner* — Navin Natnithithadha
(74) *Attorney, Agent, or Firm* — Morse, Barnes-Brown & Pendleton, P.C.; Erin E. Bryan, Esq.

(57) ABSTRACT

Embodiments of the disclosure can include systems, methods, and devices for detecting and identifying certain substances, such as volatile organic compounds (VOCs) in the exhaled breath of a subject or person in real-time using a breath analyzer device.

11 Claims, 13 Drawing Sheets

(56) References Cited

U.S. PATENT DOCUMENTS

| | | | | |
|---|---|---|---|---|
| 2003/0004426 A1* | 1/2003 | Melker | ............... | G01N 29/022 |
| | | | | 600/532 |
| 2003/0139681 A1* | 7/2003 | Melker | ............... | A61B 5/0836 |
| | | | | 600/532 |
| 2003/0176804 A1* | 9/2003 | Melker | ............... | A61M 16/01 |
| | | | | 600/532 |
| 2004/0081587 A1* | 4/2004 | Melker | ................ | A61B 5/411 |
| | | | | 422/84 |
| 2005/0065446 A1* | 3/2005 | Talton | ................ | G01N 33/497 |
| | | | | 600/529 |
| 2005/0233459 A1* | 10/2005 | Melker | ................ | A61B 5/411 |
| | | | | 436/56 |
| 2007/0062255 A1* | 3/2007 | Talton | ................ | G01N 33/497 |
| | | | | 73/23.3 |
| 2016/0371590 A1* | 12/2016 | Blackley | .............. | G01N 33/497 |
| 2017/0030882 A1* | 2/2017 | Skoda | .................. | A61M 11/041 |
| 2018/0356386 A1* | 12/2018 | Skoda | .................. | A61M 11/041 |
| 2020/0029858 A1* | 1/2020 | Reddy | .................. | A61B 5/6898 |
| 2020/0170545 A1* | 6/2020 | Reddy | ................... | G16H 40/67 |

OTHER PUBLICATIONS

Final Office Action issued in U.S. Appl. No. 16/894,746 dated Jan. 25, 2021.
U.S. Appl. No. 16/894,746, filed Jun. 5, 2020, Reddy.
U.S. Appl. No. 16/933,525, filed Jul. 20, 2020, Reddy.
U.S. Appl. No. 17/089,696, filed Nov. 4, 2020, Reddy.
U.S. Appl. No. 17/203,684, filed Mar. 16, 2021, Reddy.

* cited by examiner

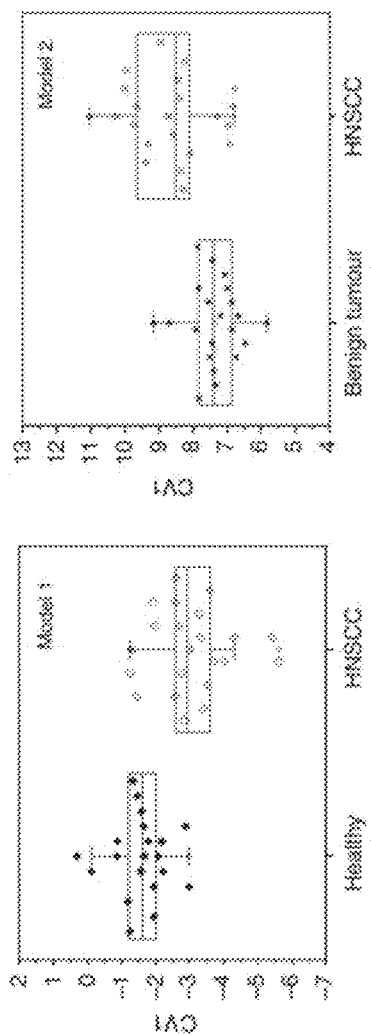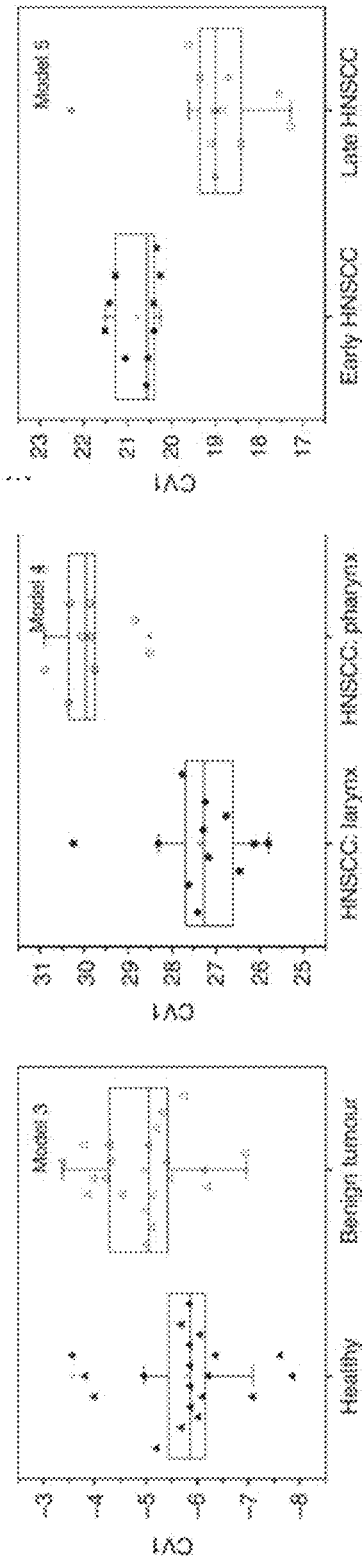
FIG. 9A
FIG. 9B
FIG. 9C
FIG. 9D
FIG. 9E

REAL TIME BREATH ANALYZER FOR DETECTING VOLATILE ORGANIC COMPOUNDS AND IDENTIFYING DISEASES OR DISORDERS

TECHNICAL FIELD

The disclosure relates particularly to systems and methods for using portable breath analyzer devices for detecting and identifying certain substances, such as volatile organic compounds (VOCs) in the exhaled breath of a subject or person in real-time. Developing novel sensors for VOC detection offers a great possibility to create a low-cost and highly sensitive sensor for disease detection and diagnosis, such as cancer, chronic obstructive pulmonary disease (COPD), rheumatoid arthritis, tuberculosis, and coronavirus disease 2019 (COVID 19).

BACKGROUND OF THE INVENTION

Every disease has associated alterations in normal physiology and metabolism and are characterized by some changes at the level of gene regulation, protein expression and metabolite production. Some of these changes can be disease specific and hence could be used as "biosignatures" for those diseases. In this sense, the occurrence of certain volatile organic compounds (VOCs) in exhaled breath as a result of alterations in various metabolic pathways can distinguish a disease state from a healthy state.

Aldehydes participate in human metabolism in various forms, such as being involved in signal transduction, gene regulation, and cellular proliferation, although some of them are cytotoxic intermediates. These compounds can be generated in the body through various mechanisms, for example metabolic conversion of alcohols is a major source of the compounds. Another mechanism for generating aldehydes is the reduction of hydroperoxide by cytochrome p450 as a secondary product of lipid peroxidation. The hydroperoxy bond undergoes a stepwise one-electron reduction, in which the first reductive step yields an alkoxy radical. This radical undergoes the well-known β-scission reaction to yield a ketone or an aldehyde and a derived radical. Additionally, smoking can generate aldehydes inside the body as by-products of tobacco metabolism mediated by cytochrome P-450 during the detoxification process. Hexanal and heptanal are another two aldehydes observed in urine, breath, and blood samples of lung cancer patients. In breast cancer patients exhale breath four aldehyde VOCs (hexanal, heptanal, octanal, and nonanal) were found to be in significantly higher concentrations when compared to healthy individuals.

Lung cancer is certainly one of the most important pulmonary diseases to study, but there are several other pulmonary complications that have been assessed using exhale breath analysis. This includes, for instance, airway inflammation, asthma, acute respiratory distress syndrome, pulmonary embolism, chronic obstructive pulmonary disease, pulmonary tuberculosis and cystic fibrosis. The common methods used in the screening of this disease are sputum smears and chest radiographs. These approaches are highly specific for active pulmonary tuberculosis, but their value in primary screening is limited by its low sensitivity and high cost. Breath VOCs might provide new biomarkers for active pulmonary tuberculosis, since, for instance, patients suffer from increased oxidative stress which creates distinct VOC patterns.

The monitoring of breath content is important, and particularly so when performing certain activities. Having a quantified analysis of volatile organic compounds (VOCs) can be useful in monitoring disease or disease treatment progression. To date, breath analyzer devices that are used to measure VOCs tend to be large and bulky. It would be advantageous to provide a VOCs measurement device that is a small sized, portable breath analyzer that overcomes the drawbacks of the prior art.

In liver diseases, breath analysis has been used to study hepatocellular carcinoma, cirrhosis, non-alcohol fatty liver disease and alcoholic hepatitis. It was possible to distinguish the breath of patients with Crohn's disease and patients with active ulcerative colitis, using GC-TOF-MS. Using SIFT-MS, Exhale breath pentane was shown to be a putative biomarker of bowel disease. In this case, however, the discriminative ability of pentane as a biomarker of bowel disease should be very limited as alkanes, namely pentane and ethane, are two very promising biomarkers of oxidative stress, which in turn is a hallmark in several diseases, including cardiovascular, oncologic and neurodegenerative diseases. Thus, an e-nose composed of an array of sensors for different exhale breath compounds that was able to discriminate patients by disease or condition with promising results would be beneficial.

Accordingly, it would be desirable to provide a portable breathalyzer device that addresses at least some of the problems identified above.

SUMMARY OF THE INVENTION

Some or all of the above needs and/or problems may be addressed by certain embodiments of the disclosure. Certain embodiments can include systems, methods, and devices for detecting and identifying certain substances, such as volatile organic compounds (VOCs) in the exhaled breath of a subject or person in real-time. In other aspects, novel sensors including coatings for various sensing elements are provided.

Disclosed herein are systems for detecting and identifying one or more volatile organic compounds (VOCs) in exhaled breath of a subject. The systems comprise a mouth piece connected to a housing, the mouth piece operable to receive the exhaled breath of the subject; a sensor module disposed in the housing, the sensor module operable to detect the one or more VOCs in the exhaled breath, and further operable to collect data associated with detection of the one or more VOCs; and a communication module disposed in the housing and in communication with the sensor module, wherein the communication module is operable to transmit collected data from the sensor module.

In some embodiments, the sensor module comprises: at least one sensor component operable to detect one or more VOCs, wherein the sensor component comprises at least one electrode, wherein the electrode is an interdigitated electrode (IDE) or a fractal electrode; and the at least one sensor component is embedded with a composite of graphite or nanomaterial allotropes of carbon in powder form and a polymer matrix with non-polar long chain hydrocarbon in powder form (sensor system 1), composite of with graphite or nanomaterial allotropes of carbon in powder form and a polymer matrix with polar hydrazine derivative and polystyrene (sensor system 2), or composite of with graphite or nanomaterial allotropes of carbon in powder form and a polymer matrix with dicyclohexyl urea and polystyrene (sensor system 3).

In some embodiments, the VOCs comprise one or more of ketone, acetone, an aldehyde, an acetaldehyde, a hydrocarbon, an alkane, a pentane, an alkene, and a fatty acid.

In some embodiments, the one more VOCs is associated with coronavirus disease 2019. In some embodiments, the VOCs comprise alkanes or alkane derivatives.

In some embodiments, the system further comprises a biomarker processing module, in communication with the sensor module, and operable to process the collected data associated with detection of the one or more VOCs and to identify the one or more VOCs. In some embodiments, the biomarker processing module is further operable to process the collected data via a neural network or pattern recognition algorithm, wherein a result from the biomarker processing module is received by the communication module for output to a mobile communication device associated with the subject. In some embodiments, the biomarker processing module is further operable to process the collected data in conjunction with other sensor data, wherein a result from the biomarker processing module is received by the communication module for output to a mobile communication device associated with the subject.

In some embodiments, the system further comprises an activity sensor operable to detect or measure one or more physical actions by the subject, and further operable to collect data associated with detection or measurement of the one or more physical actions; and wherein the communication module is in communication with the activity sensor, and the communication module is further operable to transmit collected data from the activity sensor.

In some embodiments, the communication module is further operable to communicate with a mobile communication device associated with the subject, wherein the mobile communication device receives the collected data from the sensor module and the collected data from the activity sensor. In some embodiments, the communication module is further operable to transmit collected data via at least one of the following: infrared (IR) communication, wireless communication, a Bluetooth protocol wireless communication, a direct wired connection, or to a remote memory storage device.

Also disclosed herein are methods comprising receiving an exhaled breath of the subject; detecting, via at least one sensor component, one or more VOCs in the exhaled breath; based at least in part on detection of the one or more VOCs, generating an electronic signal associated with a concentration or amount of the one or more VOCs; and outputting, via a display device, an indication of a health condition or disease associated with the concentration or amount of the one or more VOCs.

In some embodiments, the methods further comprise determining that the electronic signal correlates with a predefined signal or signal pattern associated with a health condition or disease; and identifying, based at least in part on the determination of a correlation with a predefined signal or signal pattern, a health condition or disease in the subject.

In some embodiments, the methods further comprise processing the electronic signal via a neural network or pattern recognition algorithm, wherein the electronic signal correlates with a predefined signal or signal pattern associated with a health condition or disease; and identifying, based at least in part on the determination of a correlation with a predefined signal or signal pattern, a health condition or disease in the subject.

In some embodiments, the methods further comprise classifying the electronic signal as a new signal or signal pattern associated with the health condition or disease; and storing the new signal or signal pattern in a data storage device.

In some embodiments, the methods further comprise facilitating a treatment for the subject to address the health condition or disease. In some embodiments, the health condition or disease is COVID 19.

Also disclosed herein are sensors comprising a first sensor component operable to expose one or more sensing elements to at least one volatile organic compound (VOC) in an exhaled breath of a subject, wherein the one or more sensing elements are operable to react to a presence of or contact with the at least one VOC; a second sensor component operable to generate an electronic signal when the one or more sensing elements react to the presence of or contact with the at least one VOC, wherein the electronic signal is associated with a concentration or amount of the at least one VOC; and an electronic circuit operable to transmit the electronic signal to an output device or computer processor.

In some embodiments, the first sensor component and the second sensor component each comprise at least one electrode, wherein the at least one electrode is an interdigitated electrode and/or a fractal electrode; and the first sensor component and/or the second sensor component is embedded with composite of with graphite or nanomaterial allotropes of carbon in powder form and a polymer matrix with non-polar long chain hydrocarbon powder (sensor system 1), composite of graphite with graphite or nanomaterial allotropes of carbon in powder form and a polymer matrix with polar hydrazine derivative and polystyrene (sensor system 2), or composite of with graphite or nanomaterial allotropes of carbon in powder form powder and a polymer matrix with dicyclohexyl urea and polystyrene (sensor system 3).

In some embodiments, the VOCs comprise at least one of the following: a ketone, acetone, an aldehyde, an acetaldehyde, a hydrocarbon, an alkane, a pentane, an alkene, or a fatty acid.

Disclosed herein are methods of diagnosing a subject with COVID 19, comprising receiving an exhaled breath of the subject; detecting, via at least one sensor component, one or more VOCs in the exhaled breath, wherein the one or more VOCs include alkanes; based at least in part on detection of the one or more VOCs, generating an electronic signal associated with a concentration or amount of the one or more VOCs; determining that the electronic signal correlates with a predefined signal or signal pattern associated with COVID 19; and outputting, via a display device, an indication of a positive or negative test result for COVID 19 associated with the concentration or amount of the one or more VOCs.

Disclosed herein are portable devices or systems for detecting and identifying volatile organic compounds in the breath of a subject. In some embodiments, the device includes a mouth piece connected to a housing, the mouth piece operable to receive the exhaled breath of a subject, a sensor module disposed in the housing, which collects data that detects and identifies one or more volatile organic compounds (VOCs) in the exhaled breath of the subject, and a communication module disposed in the housing connected to and in communication with the sensor module. In some embodiments, the communication module can transmit the data collected by the sensor module to an external processing apparatus. In some embodiments, the device further includes a battery disposed in the housing connected to the sensor module and the communication module. In some embodiments, an external processing apparatus is electrically or wirelessly connected to the communication module, which analyzes data transmitted by the communication module to detect and identify the volatile organic compounds in the breath of the subject.

In some embodiments, the sensor module comprises at least one sensor component operable to detect one or more VOCs. In some embodiments, the sensor component comprises an interdigitated electrode or a fractal electrode and a composite of graphite powder with tetracosane powder (sensor system 1), composite of graphite powder with polar hydrazine derivative and polystyrene (sensor system 2), or composite of graphite powder with dicyclohexyl urea and polystyrene (sensor system 3). In some embodiments, the sensor module comprises at least one array of respective sensors, wherein each sensor is operable to detect at least one VOC. In some embodiments, sensor system 1 detects alkanes, sensor system 2 detects aldehydes and alcohols, and sensor system 3 detects ketones.

In some embodiments, the one or more VOCs are associated with a health condition comprising at least one of the following: diabetes, high or low blood glucose levels, ketoacidosis, lung cancer, breast cancer, a digestive cancer, gastric cancer, peptic ulcer, colorectal cancer, prostate cancer, head-and-neck cancer, stomach cancer, liver cancer, kidney disease, or neurodegenerative disease.

In some embodiments, the device further comprises a biomarker processing module, in communication with the sensor module, and operable to process the collected data associated with detection of the one or more VOCs and to identify the one or more VOCs. In some embodiments, the biomarker processing module is further operable to process the collected data via a neural network or pattern recognition algorithm, wherein a result from the biomarker processing module is received by the communication module for output to a mobile communication device associated with the subject. In some embodiments, the biomarker processing module is further operable to process the collected data in conjunction with other sensor data, wherein a result from the biomarker processing module is received by the communication module for output to a mobile communication device associated with the subject.

In some embodiments, the device or system further comprises an activity sensor operable to detect or measure one or more physical actions by the subject, and further operable to collect data associated with detection or measurement of the one or more physical actions; and wherein the communication module is in communication with the activity sensor, and the communication module is further operable to transmit collected data from the activity sensor.

In some embodiments, the communication module is further operable to communicate with a mobile communication device associated with the subject, wherein the mobile communication device receives the collected data from the sensor module and the collected data from the activity sensor. In some embodiments, the communication module is further operable to transmit collected data via at least one of the following: IR (infrared) communication, wireless communication, a Bluetooth protocol wireless communication, a direct wired connection, or to a remote memory storage device.

Also disclosed herein are methods comprising receiving an exhaled breath of the subject; detecting, via various sensor, one or more VOCs in the exhaled breath; based at least in part on detection of the one or more VOCs, generating an electronic signal associated with a concentration or amount of the one or more VOCs; and outputting, via a display device, an indication of a health condition or disease associated with the concentration or amount of the one or more VOCs.

In some embodiments, methods further include determining the electronic signal correlates with a predefined signal or signal pattern associated with a health condition or disease; and identifying, based at least in part on the determination of a correlation with a predefined signal or signal pattern, a health condition or disease.

In some embodiments, the methods further include processing the electronic signal via a neural network or pattern recognition algorithm, wherein the electronic signal correlates with a predefined signal or signal pattern associated with a health condition or disease; and identifying, based at least in part on the determination of a correlation with a predefined signal or signal pattern, a health condition or disease.

In some embodiments, the methods further include classifying the electronic signal as a new signal or signal pattern associated with the health condition or disease; and storing the new pattern in a data storage device.

In some embodiments, the methods further include facilitating a treatment for the subject to address the health condition or disease.

Also disclosed herein are sensors comprising a first sensor component operable to expose one or more sensing elements to at least one VOC (volatile organic compound) in an exhaled breath of a subject, wherein the one or more sensing elements are operable to react to a presence of or contact with the at least one VOCs; a second sensor component operable to generate an electronic signal when the one or more sensing element react to the presence of or contact with the at least one VOC, wherein the electronic signal is associated with a concentration or amount of the at least one VOC; and an electronic circuit operable to transmit the electronic signal to an output device or computer processor.

In some embodiments, the sensor array component comprises at least one of the sensor system 1, sensor system 2, or sensor system 3. In some embodiments, the VOCs comprise at least one of the following: a ketone, acetone, an aldehyde, an acetaldehyde, a hydrocarbon, an alkane, a pentane, an alkene, or a fatty acid.

In another aspect, a method for detecting and identifying volatile organic compounds in the breath of a subject is provided. The method includes transmitting the breath of a subject collected in a mouthpiece to a housing, where the housing includes a sensor module, a communication apparatus and a battery, collecting data about the identity of the compound with the sensor module, transmitting the data with the communication apparatus to a processing apparatus and analyzing the communicated data with the processing apparatus to detect and identify the one or more compounds in the breath of the subject.

Also disclosed herein are sensor electrodes with a unique geometrical configuration that may be an interdigitated and/or fractal design.

According to yet to another embodiment, there is disclosed a coating for a sensor tray with different sensing elements embedded in the graphite powder and a polymer matrix.

In some aspects, a sensor tray is provided. The sensor system 1 includes an interdigitated or fractal electrode which includes long chain hydrocarbons in powder form with graphite or nanomaterial allotropes of carbon in powder form and a polymer matrix in which the electrodes are disposed.

In other aspects, a sensor tray is provided. The sensor system 2 includes an interdigitated or fractal electrode which includes polar molecules such as hydrazine derivatives with graphite or nanomaterial allotropes of carbon in powder form powder and a polymer matrix in which the electrodes are disposed.

In still other aspects, a sensor tray is provided. The sensor system 3 includes an interdigitated or fractal electrode which includes N,N'-dicyclohexyl urea with graphite or nanomaterial allotropes of carbon in powder form and a polymer matrix in which the electrodes are disposed.

The aspects of the disclosed embodiments generally relate to breath analyzer devices for detecting and identifying certain substances, such as VOCs, in the exhaled breath of a subject or person in real-time for disclosed embodiments. The breath analyzer devices disclosed herein may include novel sensors. In some aspects, the sensor electrodes have a special or unique geometrical configuration that is interdigitated and/or fractal in design.

Other embodiments, systems, methods, devices, aspects, and features of the disclosure will become apparent to those skilled in the art from the following detailed description, the accompanying drawings, and the appended claims.

BRIEF DESCRIPTION OF THE FIGURES

The patent or application file contains at least one drawing executed in color. Copies of this patent or patent application publication with color drawings will be provided by the Office upon request and payment of the necessary fee.

In the following, the invention will be explained in more detail with reference to the example embodiments shown in the drawings, in which:

FIG. 1A provides an architectural view of the device described herein. FIGS. 1B-1C provide a schematic of a sensor module, according to one embodiment of the disclosure.

FIG. 2A provides a schematic of an interdigitated electrode sensor, according to one embodiment of the disclosure. FIG. 2B provides a schematic of a fractal electrode sensor, according to one embodiment of the disclosure.

FIGS. 9A-9D provide predictive discriminant function analysis (DFA) models for distinguishing: head and neck cancer patients from healthy (tumor-free) subjects (FIG. 9A), head and neck cancer from benign tumor patients (FIG. 9B), benign tumor patients from healthy subjects (FIG. 9C), larynx malignancy from pharynx malignancy (FIG. 9D), and early head and neck cancer from late head and neck cancer (FIG. 9E).

Figure 1A:
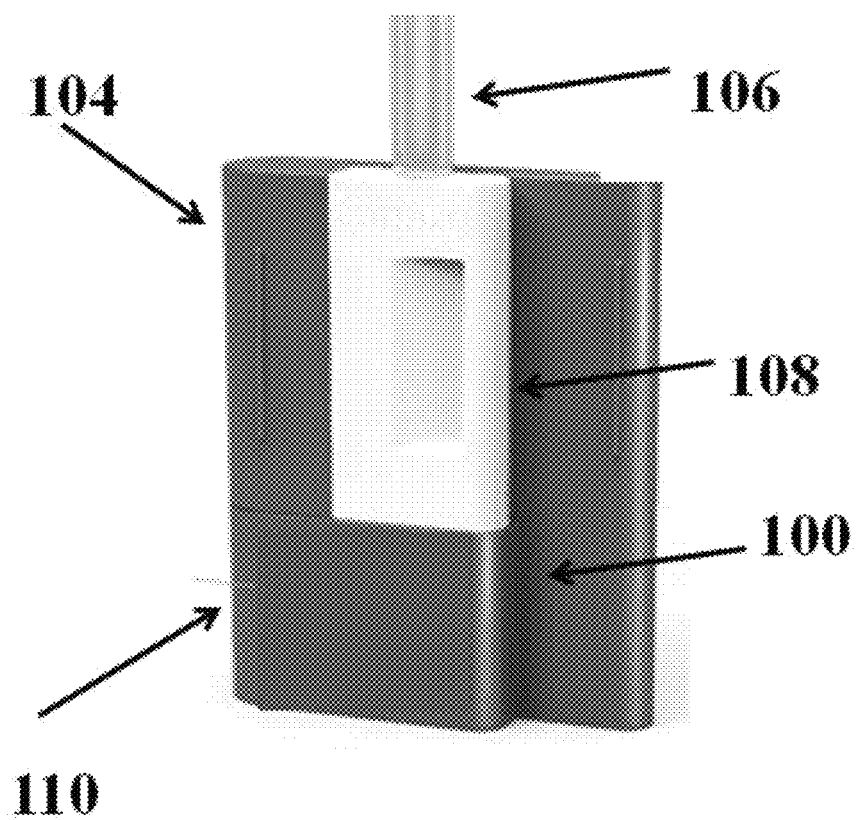
FIGS. 1A-1C depicts an example system and device for detecting certain substances including VOCs, according to one embodiment of the disclosure.

The following detailed description includes references to the accompanying drawings, which form part of the detailed description. The drawings depict illustrations, in accordance with example embodiments. These example embodiments, which are also referred to herein as "examples," are described in enough detail to enable those skilled in the art to practice the present subject matter. The example embodiments may be combined, other embodiments may be utilized, or structural, logical, and electrical changes may be made, without departing from the scope of the claimed subject matter. The following detailed description is, therefore, not to be taken in a limiting sense, and the scope is defined by the appended claims and their equivalents.

DETAILED DESCRIPTION OF THE INVENTION

Illustrated embodiments herein are directed to systems, methods, and devices for detecting and identifying certain substances, such as volatile organic compounds (VOCs) in the exhaled breath of a subject or person in real-time. Further, certain embodiments of the disclosure can be directed to systems, methods, and devices for exercise monitoring and diet management of a subject or person.

Technical effects of certain embodiments of the disclosure may include providing diagnosis and treatment for particular health conditions related to the detection and identification of certain substances, such as volatile organic compounds (VOCs) in the exhaled breath of a subject or person in real-time.

Novel sensor technology, such as nanocompositions with sensing elements, can be combined with mobile communication devices, such as smart phones, and cloud computing to create technical solutions for respiratory analysis, diagnosis, and subsequent treatment.

In some embodiments, novel sensors, such as those described herein, used in combination with the processor of a smart phone and/or remote server, and a biomarker processing module or engine with a neural network or pattern matching algorithm, can be used to detect VOCs exhaled by persons or mammals in their breath.

The detection and measurement of VOCs and other substances can be specifically correlated with certain health conditions or disease, such as, but not limited to cancer, e.g., lung cancer, breast cancer, digestive cancers, head and neck cancers, diabetes, ulcers, e.g., peptic ulcers, sepsis, infectious diseases, e.g., COVID 19, acute asthma, hepatic coma, rheumatoid arthritis, schizophrenia, ketosis, cardiopulmonary disease, e.g., chronic obstructive pulmonary disease (COPD), tuberculosis, uremia, diabetes mellitus, dysgeusia/dysosmia, cystinuria, cirrhosis, histidinemia, tyrosinemia, halitosis, and phenylketonuria, or levels of exhaled anesthetic gases used in medical procedures for surgery. Embodiments of the disclosure can have many useful and valuable applications in the biomedical industries, health care and medical care sectors.

As used herein, "biomarker" refers to signal and signal patterns associated with concentrations or amounts of certain substances, e.g., specific VOCs, associated with diagnosing or treating a health condition or disease.

In some embodiments, the real-time processing of the input by the neural network may have a slight time delay associated with converting the sensed exhaled gas to an electrical signal for an input to the neural network; however, any such delay may typically be less than 1 minute and usually no more than a few seconds.

One skilled in the art will recognize that various embodiments of the disclosure discuss the analysis of exhaled gases, although certain embodiments of the disclosure can also be used for the analysis of inhaled gases and the monitoring of pollutants or environmental effects.

FIG. 1A depicts an example system and device 102 for detecting and identifying certain substances in an exhaled breath of a subject. The example device 102, as shown in FIG. 1, can include a housing 104 which includes a mouth piece 106, a sensor module 108, and a communication module 110. The device 102 can be a handheld structure mounted to a smart phone or could be a standalone structure, which as needed could be a portable structure.

In any instance, the housing 104 can include a mouth piece 106 operable to receive an exhaled breath from a subject. For example, a person can insert the mouth piece 106 in his or her mouth, closing his or her lips around the mouth piece 106, and the person can breathe into the mouth piece, thus exhaling his or her breath into the mouth piece 106. The mouth piece 106 can include an inlet opening to receive the exhaled breath from the subject, and can further include an adjacent flow path, wherein the exhaled breath can, when received from the mouth piece, travel towards the sensor module 108.

In at least one embodiment, the mouth piece 106 can be operable to permit a subject to inhale and exhale into the housing 104 without adversely or substantially affecting the one or more samples of exhaled breath from the subject.

In at least one embodiment, a housing, such as 104, can include a sensor chamber disposed between the mouth piece 106 and a first end. For example, the sensor chamber may be a concentric-shaped chamber surrounding the flow path between the mouth piece 106 and the first end. An alkane sensor, for instance, may be positioned within the sensor chamber, wherein the alkane sensor, upon detection of an alkane in an exhaled breath within the flow path, can generate a signal correlated with an alkane concentration and/or amount in the exhaled breath.

Generally, the housing 104 can be operable to mount to or otherwise can communicate with a mobile communication device, such as a smart phone, tablet, laptop, computer, a wearable computing device, a smart watch, a wearable activity tracker, or other wireless communication or computing device. The housing may adhere to or otherwise may be relatively close proximity to the mobile communication device, wherein the communication module 110 can facilitate communications between the housing and the mobile communication device via a wireless communication technique or protocol, such as infrared (IR) communication, cellular communication, Bluetooth, or WiFi.

Figure 1B:
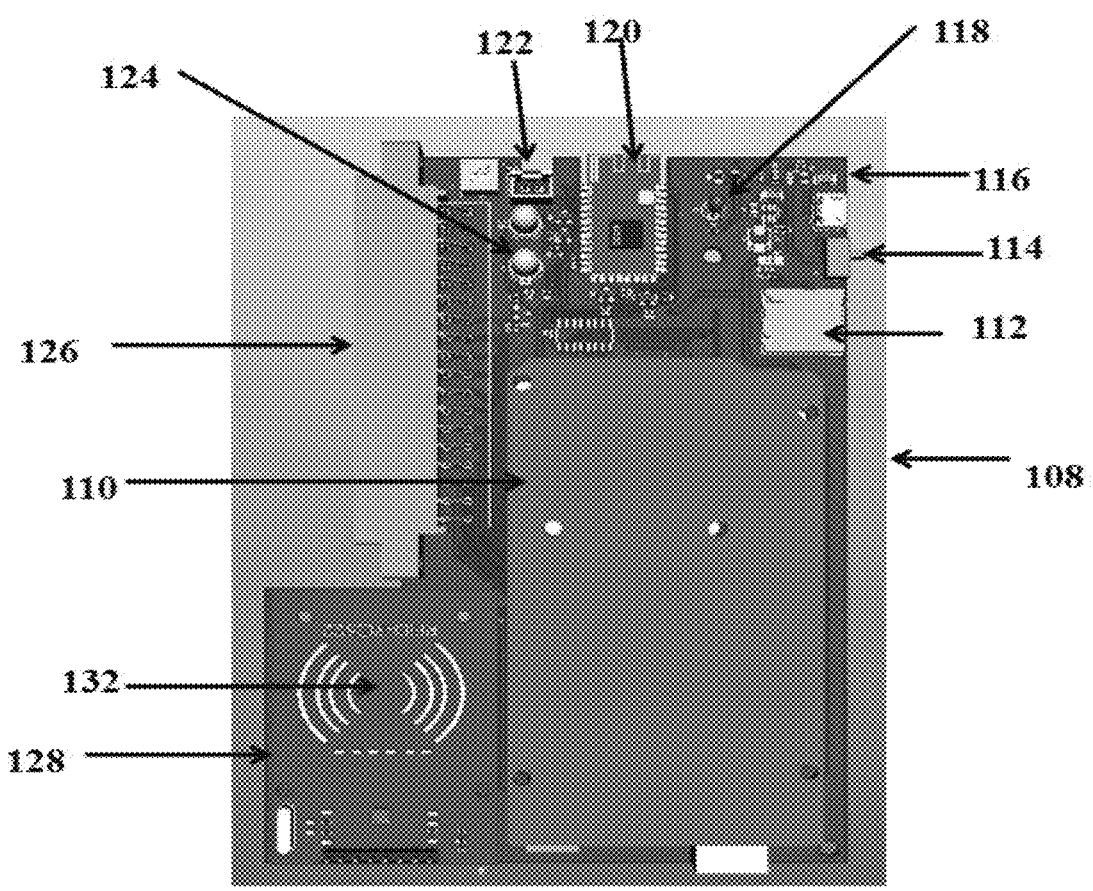

FIG. 1B shows sensor module 108 of device 102, e.g., a real time breath analyzer. Sensor module 108 includes communication module 110, which acts as the main controller of the system which performs resistance measurement processing using other peripheral circuits. SD card memory device 112 stores the data processed by communication module 110. Memory device 112 is connected to, and can be addressed by, communication module 110. On/off switch 114 can be used to turn device 102 on and off. All device operation can be controlled by switch 114. Charging port 116 is a battery charging micro USB type A port, which can be used to charge the battery from external AC/DC source. A 5V 2A DC adapter can be used to charge the battery. Indication LED 118 shows the battery charging status. When charging port 116 is plugged in with a DC adapter, indication LED 118 glows and indicates charging activity. Bluetooth communication device 120 is connected to communication module 110 and can wirelessly transfer data when successive readings have been taken. Battery connector 122 connects battery 130 with a circuit to provide a power source. Indication LEDs 124 are used to provide device operation signals. A first LED is used to show battery level indication. A second LED is used to show device operation confirmation or error indication. After successful data measurement, the LED can glow green in color, alternatively, if there is an error, the LED can glow with different colors to show the error message.

Edge slot connector 126 is used to connect a sensor tray with a main control board. The sensor tray can be the electrode configuration system which is used for resistance measurements. Any sensor tray identification can be done by RFID module 128. RFID reader reads the RFID tag fixed on the sensor tray. The RFID reader has a range of 0-3 cm above RFID antenna 132, which can be used to detect the RFID tag stickered on a sensor tray. Any passive RFID tag that appears in this range can be detected and the data that is read can be transferred to communication module 110. The RFID reader is a wireless device that can operate on the frequency range of 13.56 MHz to detect the RFID tags. RFID tags having a decoding technique in which sensor tray information can be stored and readout when it is connected to a main controller board. Sensor tray serial number, sensor tray type, and manufacturing information can be obtained from the RFID tags.

Figure 1C:
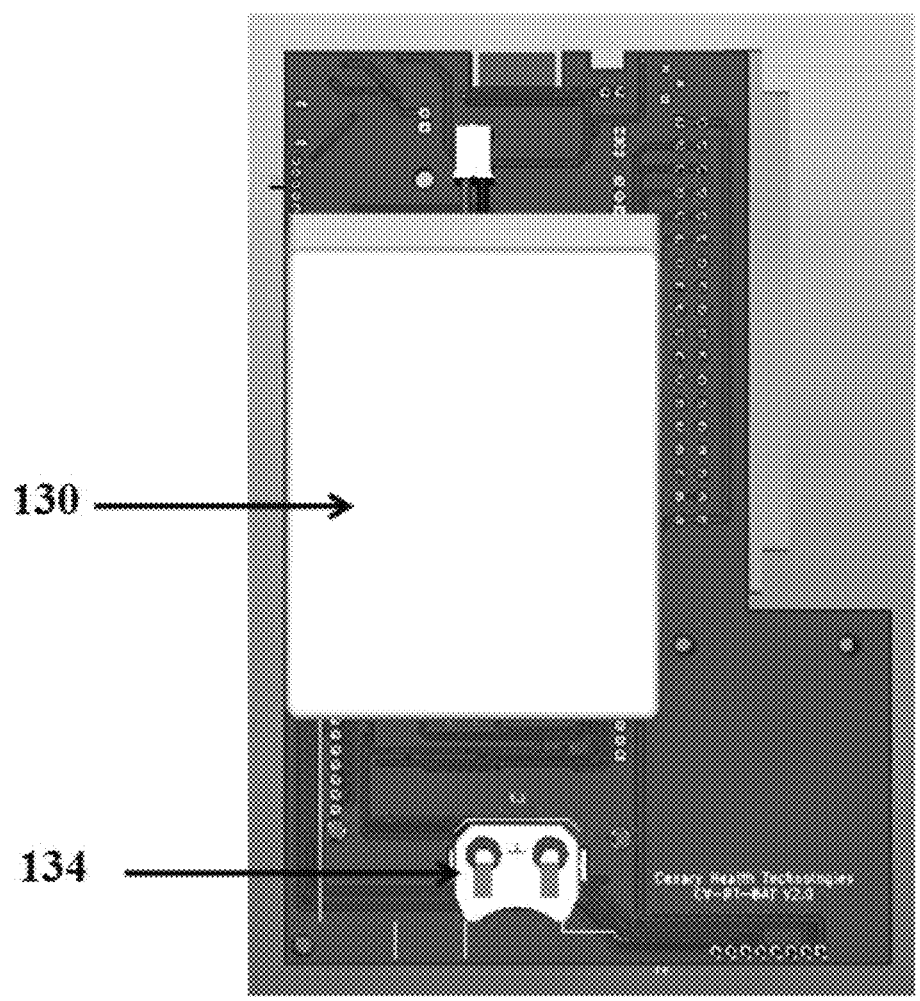

FIG. 1C provides another view of sensor module 108. Battery 130 is the main power source of device 102 and is connected to a circuit using battery connector 122. Battery 130 can be a 3.7 V 5000 mAh Lithium polymer rechargeable battery, which can have very low internal resistance and can provide long lasting performance. Using charging port 116, battery 130 can be recharged multiple times. Coin cell battery retainer 134 is made from stainless steel material which is used to hold a coin cell battery, such as CR2032. CR2032 is a 3V lithium non rechargeable battery that can be used to provide power supply to a real time clock IC even when device 102 is in an off state to maintain time and date. RTC is used to take time stamp when resistance data has been captured by the system.

In the example shown in FIG. 1A, sensor module 108 can be operable to detect certain substances, such as, for instance, one or more VOCs, in the exhaled breath, and can be further operable to collect data associated with the detection of the substances. Sensor module 108 can include at least one sensor component operable to detect at least one substance, for instance, a VOC. Depending on the specific substance to be detected and/or identified, any number of sensors and/or sensor components can be selected and/or designed to provide suitable sensitivity for detecting and identifying the specific substance as well as providing for suitable detection and/or identification of a relative concentration or amount of the specific substance. Suitable sensors and sensor components can include, but are not limited to, electronic sensors, electromechanical sensors, electrochemical sensors, or any other sensing device or technique that can convert detection of certain substances in the exhaled breath to an electrical signal.

In any instance, the one or more substances, can be detected and identified by sensor module 108. Thus, when the exhaled breath is received from mouth piece 106, the exhaled breath flows through, over, or otherwise adjacent to at least one sensor or sensor component of sensor module 108, which can detect and identify one or more substances in the exhaled breath. In some embodiments, sensor module 108 can, upon detection and identification of one or more substances, in the exhaled breath, generate an electronic signal correlating to a relative concentration or amount of a specific substances detected or otherwise identified in the exhaled breath. In some embodiments, any number of electronic signals may be generated by sensor module 108 depending on the number of detected and identified substances. Each of the electronic signals would correlate to a relative concentration or amount of a specific substance detected or otherwise identified in the exhaled breath of the subject.

In at least one embodiment, a sensor module, such as sensor module 108, can be customized to detect any number of volatile gas (VG) patterns identified in the one or more VOCs of the exhaled breath of the subject. For example, if a predefined VG pattern including three specific VOCs with respective threshold concentration, is associated with a health condition or disease, a sensor module, such as sensor module 108, can be customized or otherwise designed to include one or more sensors operable to detect and identify the three specific VOCs as well as detect and identify a concentration and/or amount of the respective VOCs. The predefined VG patterns can be specifically correlated with a particular health condition and/or disease, such as cancer, e.g., lung cancer, breast cancer, digestive cancers, or head and neck cancers, infectious diseases, e.g., COVID 19, rheumatoid arthritis, tuberculosis, COPD, or can be otherwise correlated with levels of exhaled anesthetic gases used for medical or surgical procedures. Different health conditions and diseases, such as cancers, emit different types and/or amounts of molecules. For example, endogenous cancer may release certain VOCs from the cancer cells and/or metabolic processes that are associated with cancer growth may release similar or other VOCs. In some embodiments, these VOCs can be transported with a subject's blood to the alveoli of the subject's lungs from where they can be exhaled as measurable smells or odorants. Therefore, cancer not only has a characteristic smell or odor, but, different cancers have different and unique smells or odors. When a pattern of a certain number and quantity (by concentration and/or amount) of substances is associated with a particular health condition or disease, the pattern can be stored by the system for subsequent processing to compare and/or match against patterns of substances detected and identified by a sensor module, such as sensor module 108, in an exhaled breath of a subject.

Figure 2A:
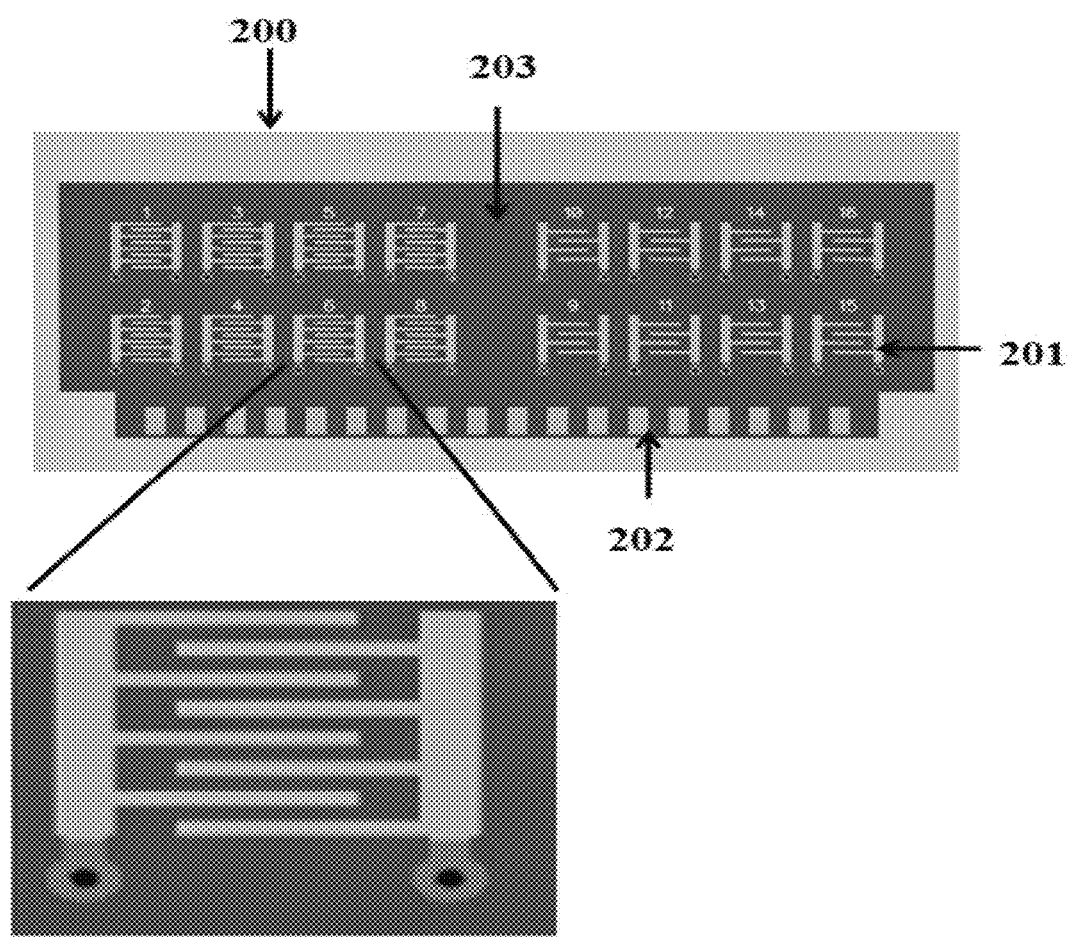
FIGS. 2A-2B depict sensors described herein.
Figure 2B:
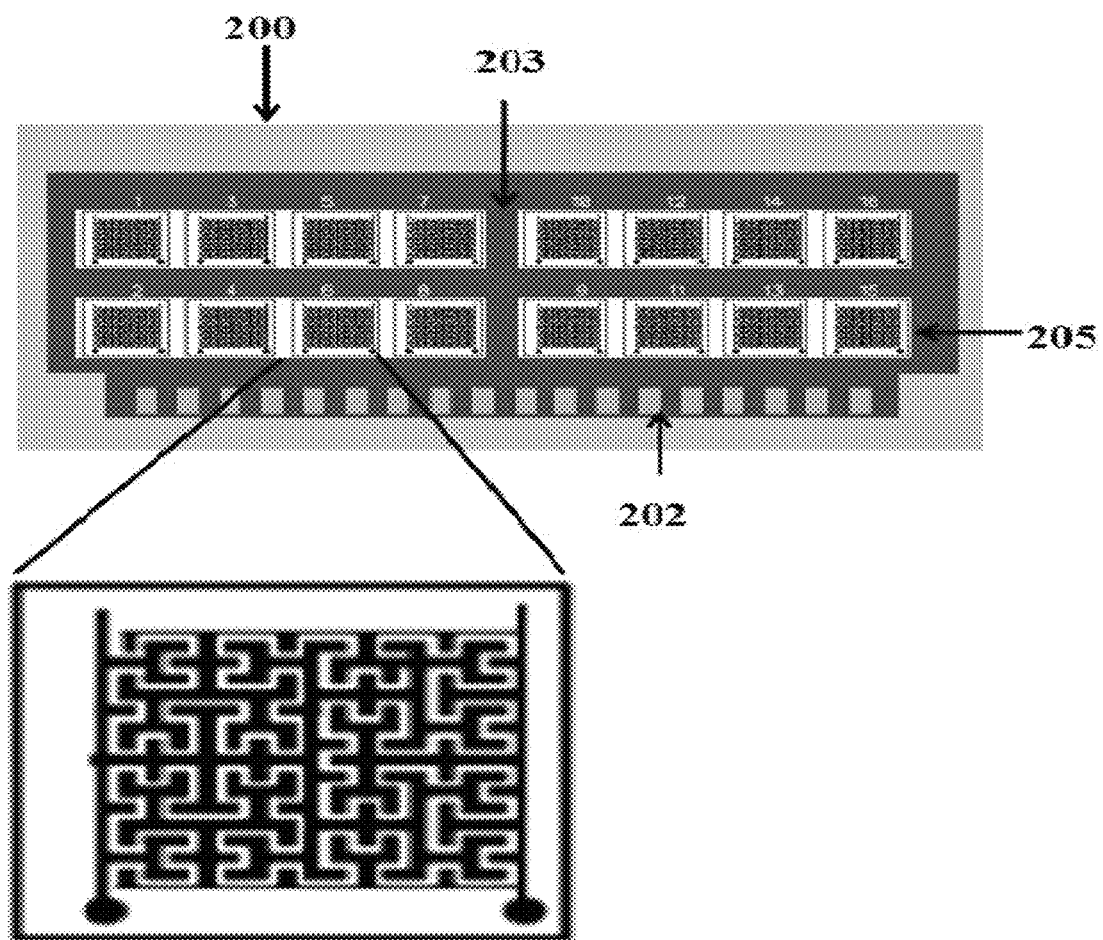

FIG. 2A and FIG. 2B illustrate a sensor component 200 having a electrodes 201 mounted on a printed circuit board (PCB) in the form of PCB tracks. In one embodiment, the electrodes 201 includes 16 electrodes. The electrodes 201 can be interdigitated electrodes 203 (FIG. 2A) or fractal electrodes 205 (FIG. 2B). In one embodiment, such as that exemplified in FIG. 2A, electrodes 201 can be configured to have a first set of electrodes (e.g., electrodes 1-8) and a second set of electrodes (electrodes 9-16). Connections 202 can be used to connect the sensor component or sensor tray 200 with a main controller board using edge slot connectors 126.

In some embodiments, alkane, such as undecane, can be detected and/or identified by a sensor module, such as sensor module 108, which can include a sensor, or sensor component, such as sensor component 200, with one or more composites with a sensing element. Any type of composite for detecting alkane, such as undecane, can be used including carbon-based composites, nanotubules, or nanofibers. In an example, the sensor component 200 shown in FIG. 2A and FIG. 2B can include sixteen interdigitated electrodes 203 and/or fractal electrodes 205. In some embodiments, a substrate can be a single-sided printed circuit board (PCB) with interdigitated/fractal built-in gold-plated copper sheets which serve as electrodes. In some embodiments, sensor elements can be deposited between the two copper sheets. Generally, due to chemoresistivity the signal response generated by a sensor component, such as sensor component 200, may be dependent on the interaction between the embedded sensing elements and the VOC. In certain aspects, due to chemical adsorption or physical adsorption at the interdigitated electrode, an electronic signal and/or signal pattern can be generated from the sensor component 200.

In some aspects, the interdigitated geometry is the most widely accepted geometry for the electrodes of a gas sensor since it enables a wide contact area between the electrodes within the limited area. In addition, it forms the electrodes first and then deposits the sensing materials on them, thereby causing no damage to the sensing materials. In some aspects, the width of digits in interdigitated electrodes or the space between the electrodes can affect the sensor performance. In other words, when the electrode spacing is narrow, the current between electrodes flows only in the film area right above it. Alternatively, when the spacing is wide, the current flows both horizontally and vertically throughout the film, thereby sampling a wider area. In addition, the electrode-semiconductor interface itself can cause a change in the device sensitive resistance. When the width/gap ratio of the electrode is changed, the influence of both the interface and the film resistance on sensitivity can be relatively reduced. It has been observed through simulations that there is an increase in the sensitivity following an increase in the spacing between the electrodes when the electrodes were placed under a sensing film if the sensor was very sensitive to the gas. In contrast, when an electrode was placed above the sensing film, the sensor sensitivity decreases as the spacing between the electrodes increased.

In other aspects, the fractal geometry in one in which fractal breaks the barrier of traditional Euclidean geometry. When it comes to a dimension, people intuitively think of a line or a curve as a typical one-dimensional object and a plane as a typical two-dimensional object. Fractal geometry shows a line segment can also be two-dimensional and can fill the entire plane. Such a fractal curve, which is based on fractal geometry theory, provides new ideas for the design and manufacture of high performance of gas sensors, due to its special structure and dimensions compared to conventional Euclidean geometry. For the sensors described herein, the fractal dimension provides a basis for the manufacture of ultra high surface area electrodes which maximize charge density. Secondly If the parallel plates are paired laterally they will store more energy and will produce a bigger capacitance. As the capacitance increases, changes in gas concentration can result in larger sensor responses, which in turn increase sensor sensitivity.

Figure 3:
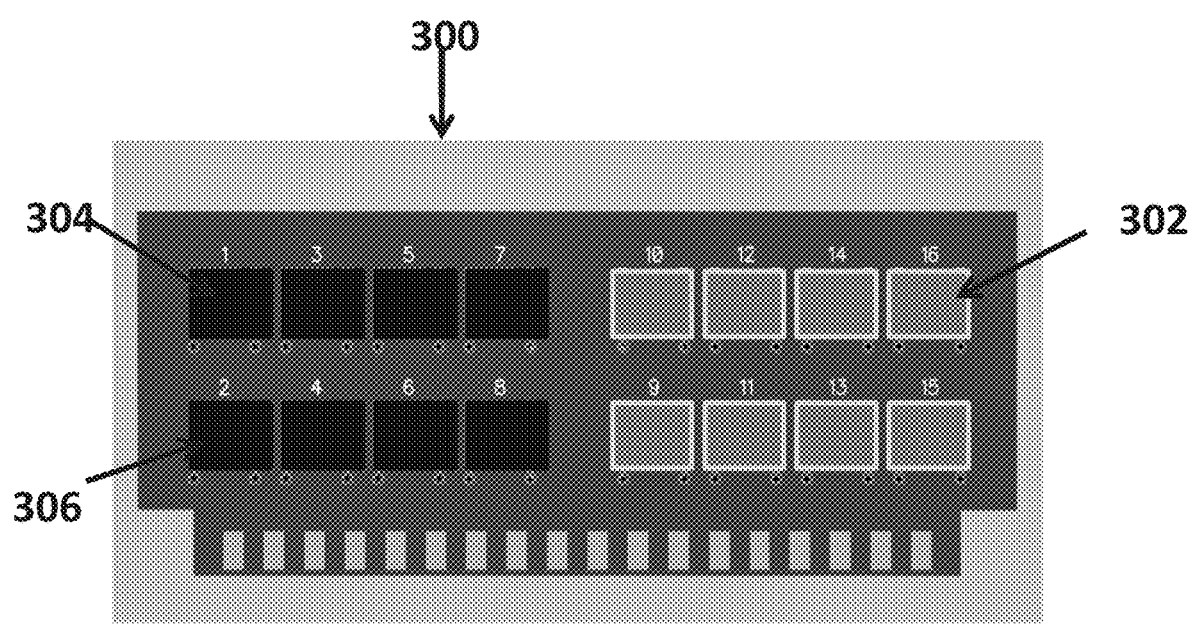
FIG. 3 depicts a schematic view of a sensor module device for detecting certain substances including sensing elements, according to one embodiment of the disclosure.

In some embodiments, certain substances, such as VOCs, can be detected and identified using a sensor module, such as sensor module 108, which can include a sensor or sensor component, such as sensor component 300 as shown in FIG. 3. Sensor component 300 can be embedded with fused non-polar long chain hydrocarbon in powder form and graphite or allotropes of carbon nanomaterial in powder composite 302 (also referred to herein as sensor system 1).

When the exhaled breath of a subject includes one or more VOCs, such as alkanes (e.g., undecane), and is passed through, over, or adjacent to the fused non-polar long chain hydrocarbon and graphite or allotropes of carbon nanomaterial in powder composite 302, the non-polar long chain hydrocarbon can selectively trap or physically adsorb, one or more VOCs including undecane. In this manner, the resulting trapped VOCs within the non-polar long chain hydrocarbon molecules of the fused non-polar long chain hydrocarbon and graphite or allotropes of carbon nanomaterial powder composite 302 can facilitate generating an electronic signal and/or signal pattern from sensor component 300, the signal corresponding in strength to a concentration and/or amount of the VOCs trapped within the non-polar long chain hydrocarbon of the fused non-polar long chain hydrocarbon and graphite or allotropes of carbon nanomaterial powder composite 302. The signal and/or signal pattern can be transmitted to the communication module 110 and transmitted to a mobile communication device for subsequent processing.

In some embodiments, certain substances, such as VOCs, can be detected and identified using a sensor module, such as sensor module 108, which can include a sensor or sensor component, such as sensor component 300 shown in FIG. 3. Sensor component 300 can be embedded with polar hydrazine derivatives with nanomaterial allotropes of carbon in powder form or graphite carbon powder and polystyrene composite 304 (also referred to herein as sensor system 2). When the exhaled breath of a subject includes one or more polar VOCs, such as aldehydes (e.g., hexanal), and is passed through, over, or adjacent to the polar hydrazine derivative with nanomaterial allotropes of carbon in powder form or graphite with nanomaterial allotropes of carbon in powder form or graphite carbon powder and polystyrene composite 304, the polar hydrazine derivative can selectively trap or physically adsorb, one or more VOCs including hexanal. In this manner, the resulting trapped VOCs within the polar hydrazine derivative of the polar hydrazine derivatives with nanomaterial allotropes of carbon in powder form or graphite carbon powder and polystyrene composite 304 can facilitate generating an electronic signal and/or signal pattern from the sensor component 300, the signal corresponding in strength to a concentration and/or amount of the VOCs trapped within the polar hydrazine derivative of the polar hydrazine derivative with nanomaterial allotropes of carbon in powder form or graphite carbon powder and polystyrene composite. The signal and/or signal pattern can be transmitted to the communication module 110 and transmitted to a mobile communication device for subsequent processing.

In some embodiments, certain substances, such as VOCs, can be detected and identified using a sensor module, such as sensor module 108, which can include a sensor or sensor component, such as sensor component 300 shown in FIG. 3. In some embodiments, sensor component can be embedded with N,N' dicyclohexyl urea with nanomaterial allotropes of carbon in powder form or graphite carbon powder and polystyrene composite 306 (also referred to herein as sensor system 3). When the exhaled breath of a subject includes one or more VOCs, such as carbonyl compounds (e.g., acetone), and is passed through, over, or adjacent to the N,N' dicyclohexyl urea with nanomaterial allotropes of carbon in powder form or graphite carbon powder and polystyrene composite 306, the N,N' dicyclohexyl urea can selectively trap or physically adsorb, one or more VOCs including acetone. In this manner, the resulting trapped VOCs within the N,N' dicyclohexyl urea of the N,N' dicyclohexyl urea with nanomaterial allotropes of carbon in powder form or graphite carbon powder and polystyrene composite 306 can facilitate generating an electronic signal and/or signal pattern from the sensor component 300, the signal corresponding in strength to a concentration and/or amount of the VOCs trapped within the N,N' dicyclohexyl urea of the N,N' dicyclohexyl urea with nanomaterial allotropes of carbon in powder form or graphite carbon powder and polystyrene composite. The signal and/or signal pattern can be transmitted to the communication module 110 and transmitted to a mobile communication device for subsequent processing.

In at least one embodiment, certain substances, such as VOCs, can be detected and identified using a sensor module, such as sensor module 108, which can include a sensor or sensor component, such as sensor component 300 shown in FIG. 3. In one embodiment, sensor component 300 includes sensors 1 to 4 coated with sensor system 3, sensors 5-8 coated with sensor system 2 and sensors 9 to 16 coated with sensor system 1.

In some embodiments, a sensor module, such as sensor module 108, includes polymer-based sensors for chemical vapor sensing. After exposure to chemical vapors, the active sensing materials interact with the chemical vapors, and the doping level in carbon material with polymer matrix transfers electrons to or from the analytes, causing conductivity changes. For electronic noses, the sensor module consists of various sensor elements, which can be coated with polymer materials; therefore, the sensors could exhibit different sensitivity and selectivity. A conductive polymer composite sensor, which can be fabricated by coating or encapsulating a mix of conductive and non-conductive materials on an electrode surface, can be used. In some embodiments, the polymer is the non-conductive material of a specific receptor agent; it can absorb and desorb the target in the vapor in the early and late vapor-diffusion stages. The conductive materials contribute electrical conductivity to the sensing films and the polymers swell to increase the resistance level when exposed to a vapor.

In some embodiments, a sensor module, such as sensor module 108, can include at least one sensor with at least one composite material sensor coating. In some embodiments, the sensor coating and its application to a sensor may determine the reproducibility of a sensor. For example, a uniform thin film of the sensor coating is crucial for microsensors with small active layers, allowing the film to contribute to efficient field-effect mobility and to reduce noise. Various techniques can be used to coat the chemiresistive thin film on at least one sensor, including screen printing, spin coating, spraying, ink-jet printing, and imprinting. To address the reproducibility issues with forming a uniform thin coating on a sensor, a biomimetic two-layer carbon-based polymer composite sensor was used as an example. The quality of the sensing film was easily controlled, maintaining the well sensitivity and stability.

In some embodiments, the sensor array was applied in a portable electronic nose to identify volatile organic compounds. In some aspects, the power of a sensor array can be quantized to evaluate the performance levels of sensing tasks, and an algorithm has also been proposed to estimate the ability of the sensor array to identify odor.

In at least one embodiment, a sensor module, such as sensor module 108, can include multiple sensors and/or sensor components organized into an array of sensors or a sensor array. The sensor array may include any number of particular sensors tuned to detect one or more specific substances, such as VOCs. Further, the sensor array may include any number of particular sensors tuned to increase the relative selectivity and sensitivity of the sensor array to detect and/or identify a specific amount or concentration of one or more substances, such as VOCs.

In at least one embodiment, a biomarker processing module, can be operable to process the collected data from a sensor module, such as sensor module 108, via a neural network or pattern recognition algorithm, wherein a result from the biomarker processing module can be output to a display associated with a mobile communication device. For example, when data is processed by a neural network or pattern matching algorithm, an initial result may include identification of one or more substances in the exhaled breath, identification of a unique sensor derived signal and/or signal pattern of the one or more substances in the exhaled breath, an identification of and/or correlation with a health condition or disease, and/or an identification of and/or correlation with any number of substances in a subject's exhaled breath. The biomarker processing module can, in certain instances, communicate with a diagnostic module, such as, to prepare and present a suitable output or result for transmission to the display associated with a mobile communication device.

An example neural network can be initially created and/or subsequently trained by receiving and storing any number of previously detected and identified signals and/or signal patterns of one or more substances from the exhaled breaths of any number of subjects. In some embodiments, the signals and/or signal patterns of multiple substances can be received and stored, wherein each signal and/or signal pattern may be correlated with one or more health conditions or diseases. Each signal and/or signal pattern may include a respective concentration and/or amount of any number of substances. In general, the neural network uses three different layers of neurons. The first layer is input layer, which receives data from sensor module, the second layer is hidden layer, while the third layer is output layer, which provides the results of the analysis. Note that each neuron in hidden layer is connected to each neuron in input layer and each neuron in output layer. In the exemplified neural network, hidden layer processes data received from input layer and provides the result to output layer. Any number of hidden layers may be used, with the number of neurons limited only by processing power and memory of the general purpose computer. The inputs to the input neurons are inputs from the sensors in the sensor module. In general, the number of output neurons corresponds to the number of compounds that the sensor module is trained to detect and identify. The number of hidden neurons may vary considerably.

An example pattern recognition algorithm can be an algorithm operable to seek a best match or relatively high confidence score in matching a signal and/or signal pattern to one or more previously stored signals and/or signal patterns correlated with one or more health conditions or diseases. E-noses are gas-sensing systems that generally contain cross-reactive multi-sensor arrays capable of discriminating between sensor-response patterns of VOCs by using pattern-recognition algorithms. E-nose analytical results generally are based on pattern recognition algorithms using software that compares VOCs profiles of analytes to profiles of known samples in redeveloped diagnostic libraries. The recognition process of a sample type usually is achieved through the use of pattern-recognition algorithms and specific statistical software in combination with machine neural net learning linked to smellprint reference library databases of known sample type signatures previously recorded from known healthy and diseased tissue samples from known host species.

In addition to a neural network and pattern recognition, any number of mathematical and computational tools and techniques can be implemented by a biomarker processing module to process collected data from a sensor module, such as sensor module 108, including, but not limited to, artificial intelligence techniques, a multifactorial approach, leave-one-out cross-validation (LOOCV), nonlinear support vector machine (SVM), multi-layer perception (MLP), generalized regression neural network (GRNN), fuzzy inference systems (FIS), self organizing map (SOM), radial bias function (RBF), genetic algorithms (GAS), neurofuzzy systems (NFS), adaptive resonance theory (ART) and statistical methods such as canonical discriminant analysis, canonical correlation, principal component analysis (PCA), partial least squares (PLS), multiple linear regression (MLR), principal component regression (PCR), discriminant function analysis (DFA) including linear discriminant analysis (LDA), and cluster analysis including nearest neighbor.

In at least one embodiment, one or more signals and/or signal patterns of multiple substances can be associated with type of cancers including but not limited to respective VOCs. For example, head and neck cancers (HNC) refers to a group of diverse tumors in the region of the head and neck. Most head and neck cancers (HNC) are squamous cell carcinoma of the head and neck that arise from the mucosa lining of the upper aero digestive tract. The concentration profiles of several HNC specific VOCs have been determined, mainly hydrocarbons (alkanes, alkenes, alcohols, ketones and organic acids) by proton-transfer reaction mass spectroscopy. 2-Butanone seems to be ubiquitously present and has been detected in several human fluids of apparently healthy volunteers, including skin emanations, saliva, urine, feces, blood and exhaled breath.

In some embodiments, one or more signals and/or signal patterns of multiple substances can be associated with head and neck cancer. For example, the substances and/or volatile organic compounds including, but not limited to, 2,2-dimethyl-decane, 4,6-dimethyl-dodecane, 5-methyl-3-hexanone, 2,2-dimethyl propanoic acid, limonene, undecane, ethanol, 2-propenenitrile can be associated with head and neck cancer. Certain observations in various subjects have indicated that these substances, volatile organic compounds, and combinations thereof, can be significantly elevated in subjects with head and neck cancer, as compared with subjects having less severe head and neck conditions.

FIG. 9 provides predictive discriminant function analysis (DFA) models for distinguishing (A) head and neck cancer patients from healthy (tumor-free) subjects, (B) head and neck cancer from benign tumor patients, (C) benign tumor patients from healthy subjects, (D) larynx malignancy from pharynx malignancy and (E) early head and neck cancer from late head and neck cancer. The DFA plots were obtained from the responses of three non-correlated sensing features from the same sensor. Excellent separation was achieved between head and neck squamous cell carcinoma (HNSCC) and healthy states, as well as HNSCC and benign tumors. In contrast, the benign tumors were less well-separated from the healthy states and the clusters overlapped more prominently.

In at least one embodiment, a breath sensor system, device, and associated methodology as described below can differentiate between patients with lung cancer, patients with Chronic Obstructive Pulmonary Disease (COPD), and healthy patients with no lung cancer or COPD. The breath sensor system and associated methodology can detect certain biomarkers for lung cancer and COPD. In one example, breath alkanes in a subject can increase as oxidative stress is elevated in lung cancerous cells. The alkanes exhaled in the breath of the subject can serve as biomarkers for detection of lung cancer and/or COPD as the concentration of these alkanes in a subject with cancer is relatively higher than the concentration of similar alkanes in a healthy subject.

Figure 10:
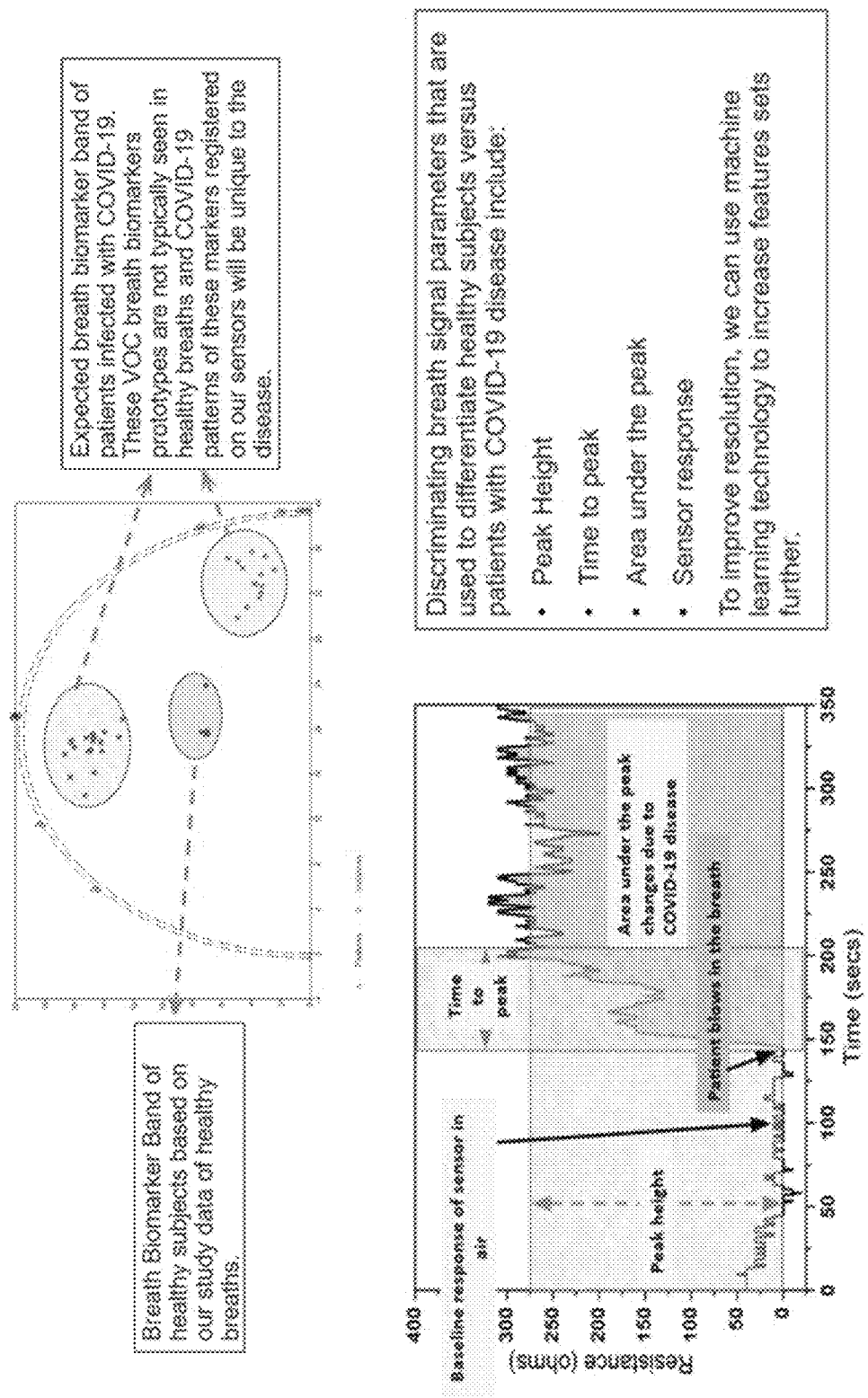
FIG. 10 shows that COVID 19-type biomarker VOCs were distinguishable and detectable using the sensor module described herein.

In some embodiments, one or more signals and/or signal patterns of multiple substances can be associated with type of infectious diseases, e.g., coronavirus disease 2019 (COVID 19) including but not limited to respective VOCs. For example, COVID-19 initiates oxidative stress by a similar mechanism observed in influenza virus pneumonia, with the production of highly reactive nitrogen oxide species, such as peroxynitrite, via interaction with oxygen radicals and reactive oxygen intermediates. This in turn enhances the concentration of alkanes and alkane derivatives that are exhaled from the breath. FIG. 10 shows that COVID 19-type biomarker VOCs were distinguishable and detectable using the sensor module described herein.

A diagnostic module, can be operable to receive processed data from the biomarker processing module and can be further operable to determine, based at least in part on the processed data from the biomarker processing module one or more diagnoses and/or treatments for a subject. The diagnostic module in some instances, via the one or more processors and/or network and I/O interface may communicate with the biomarker processing module of the device to receive processed data. In such instances, the diagnostic module can be further operable to determine, based at least in part on the processed data from the biomarker processing module, one or more diagnoses and/or treatments for a subject.

Figure 4:
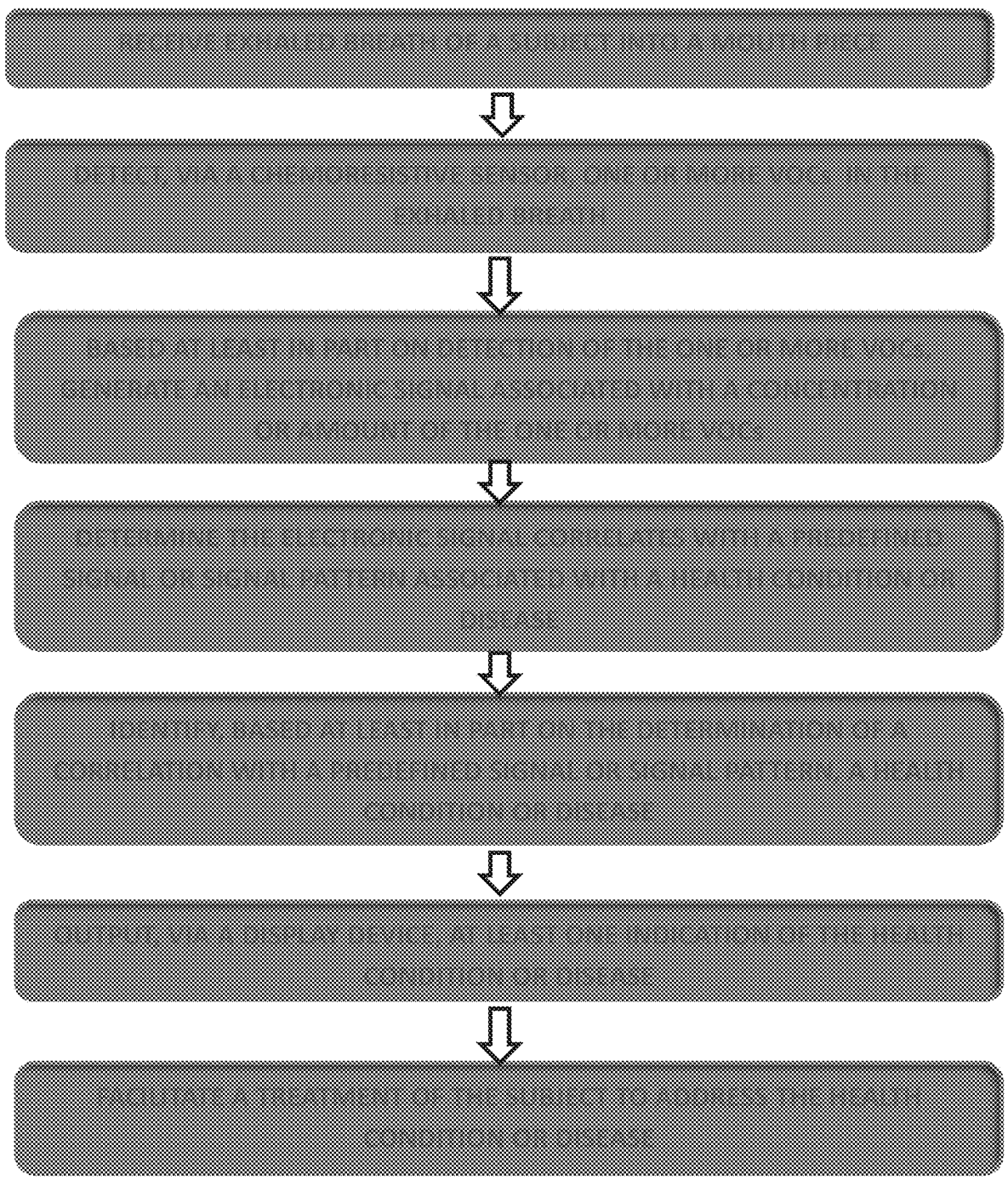
FIG. 4 depicts a flow chart of a method for detecting certain substances, including VOCs, according to one embodiment of the disclosure.

FIG. 4 depicts a flow chart of a method for detecting certain substances including VOCs, according to one example embodiment of the disclosure. In some embodiments, a method of identifying a subject as having a disease or condition or of monitoring the progression of a disease or condition in a subject comprises receiving exhaled breath of a subject into a mouth piece of a device; detecting, via at least one sensor component, one or more VOCs in the exhaled breath; based at least in part on the detection of the one or more VOCs, generating an electronic signal associated with a concentration or amount of the one or more VOCs; determining that the electronic signal correlates with a predefined signal or signal pattern associated with a health condition or disease; and outputting, via a display device, at least one indication of a positive or negative indication of a health condition or disease. In some embodiments, treatment is administered to the subject identified as having a health condition or disease.

In some embodiments, the device described herein is used to diagnose a subject with cancer, e.g., lung cancer or head and neck cancer. In other embodiments, the device described herein is used to diagnose a subject with an infectious disease, e.g., COVID 19. In still other embodiments, the device described herein is used to diagnose a subject with rheumatoid arthritis. In other embodiments, the device described herein is used to diagnose a subject with tuberculosis. In some embodiments, the device described herein is used to diagnose a subject with COPD.

In some embodiments, the methods described herein may be used to monitor progression of a health condition or disease in a subject. For example, after treatment is administered or while treatment is ongoing, one or more VOC levels may be monitored using the device described herein. As the one or more VOC levels decrease it is expected that the subject is responding to treatment and is improving in health. In some embodiments, a subject identified as having COVID 19 is undergoing treatment and as the subject responds to treatment one or more VOC levels, such as alkane or alkane derivative levels, will decrease.

In some embodiments, a method of treating a patient for cancer can include determining, based at least in part on expression levels of one or more biomarkers in a sample of exhaled breath from the patient that the patient is responding positively or negatively to a cancer treatment regime. If the patient is not responding favorably, e.g., the one or more biomarkers are not decreasing, the cancer treatment regime may be adjusted.

Figure 5:
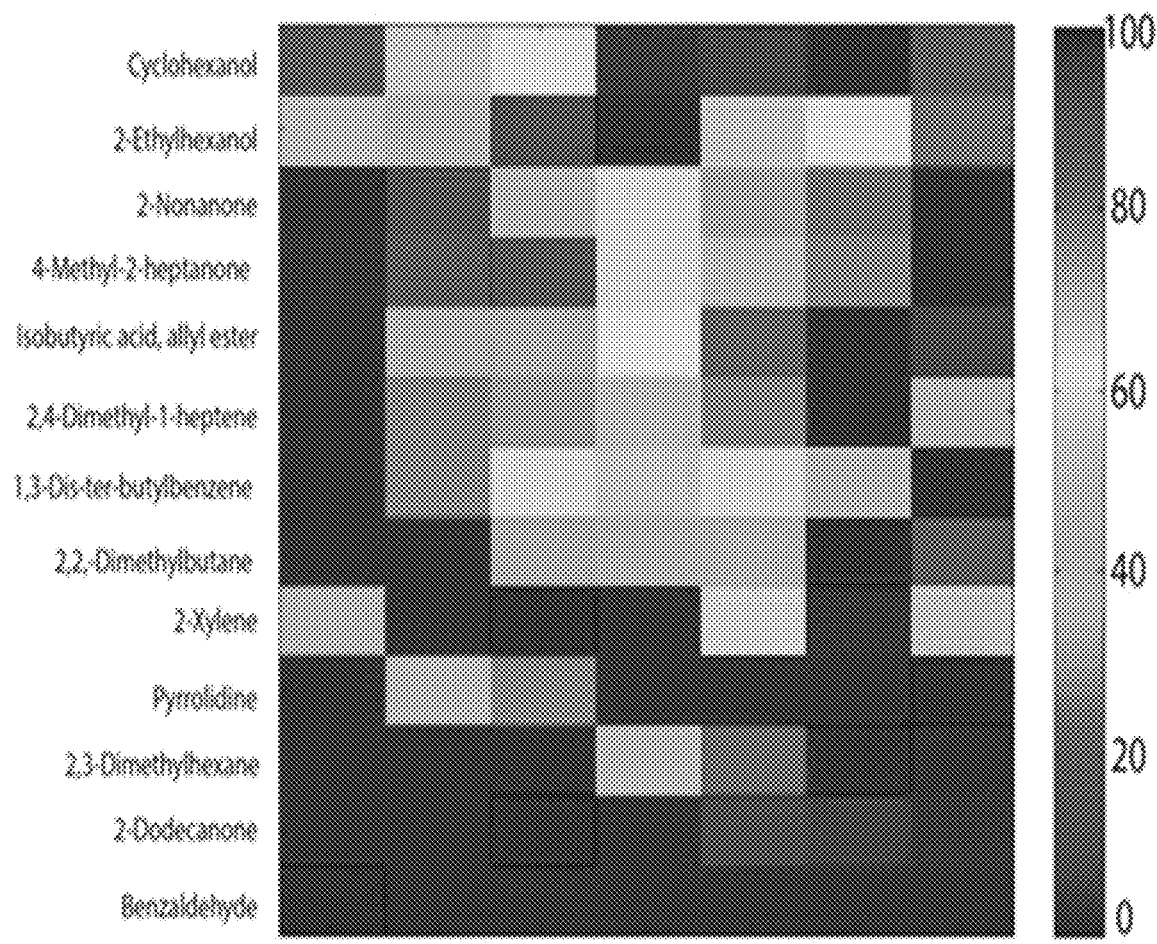
FIG. 5 depicts an example heat map graphic generated by a biomarker processing module or engine, according to one embodiment of the disclosure.

FIG. 5 provides example heat map graphics, which were generated by a biomarker processing module or engine, according to one example embodiment of the disclosure. In the heat map graphic, the vertical axis illustrates a number of substances, such as VOCs, which were tested in an exhaled breath of one or more samples or subjects. The horizontal axis illustrates a number of samples, including at least one control and a number of uniquely identified samples. In any instance, the vertical heat bar ranging from 0 to 100, illustrates a range of color values for which each of the substances was detected and identified in the exhaled breaths of each of the tested samples. Thus, a respective shade of the color values corresponds with a concentration and/or amount of a substance detected and identified in the exhaled breath samples. For example, a relatively low concentration and/or amount can appear as a blue color corresponding to about 0 to 40, a relatively medium concentration and/or amount can appear as a green to light yellow color corresponding to about 40 to 60, a upper medium concentration and/or amount can appear as a dark yellow to light orange color corresponding to about 60 to 80, and a relatively high concentration and/or amount can appear as a dark orange color to red color corresponding to about 80 to 100. In this manner, an observer can readily evaluate data presented in the heat map graphic to determine which substances have a relatively low and/or high concentration and/or amount for a particular subject or sample.

Figure 6:
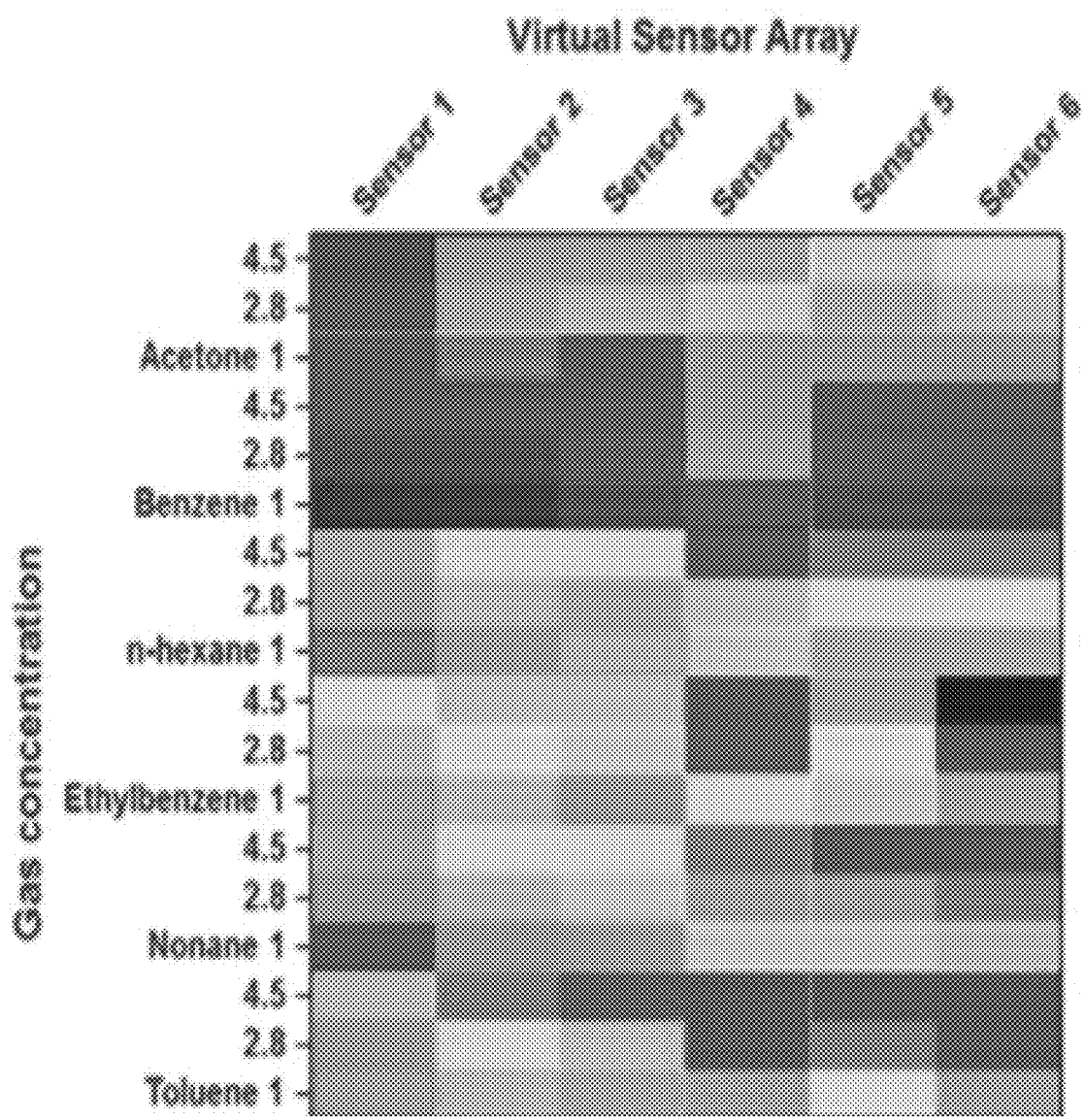
FIG. 6 depicts an example heat map graphic generated by a biomarker processing module or engine, according to one embodiment of the disclosure.

FIG. 6 depicts another example heat map graphic generated by a biomarker processing module or engine, according to one example embodiment of the disclosure. Similar to the graphic of FIG. 5, in this heat map graphic shown in FIG. 6, the vertical axis illustrates a number of substances, such as VOCs, which were tested in an exhaled breath of one or more samples or subjects. The horizontal axis illustrates a number of sensors, but for different health conditions, such as lung cancer, pancreatic cancer, and breast cancer, and a normal or control sample. In any instance, the range of color values for which each of the substances was detected and identified in the exhaled breaths of each of the tested samples. Thus, a respective shade of the color values corresponds with a concentration and/or amount of a substance detected and identified in the exhaled breath samples.

Figure 7:
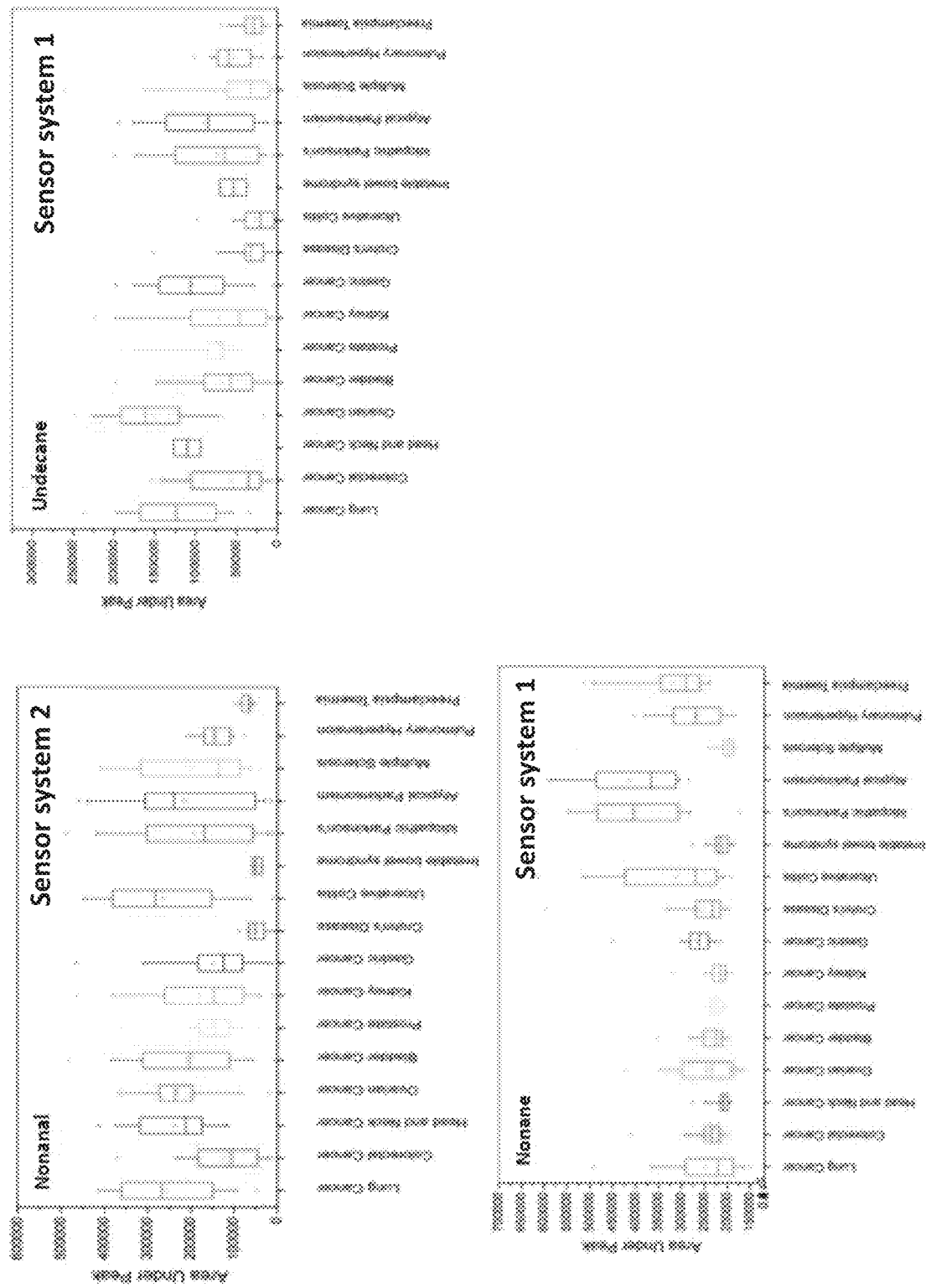
FIG. 7 depicts an example of a user interface output by a diagnostic module, according to one embodiment of the disclosure
Figure 8:
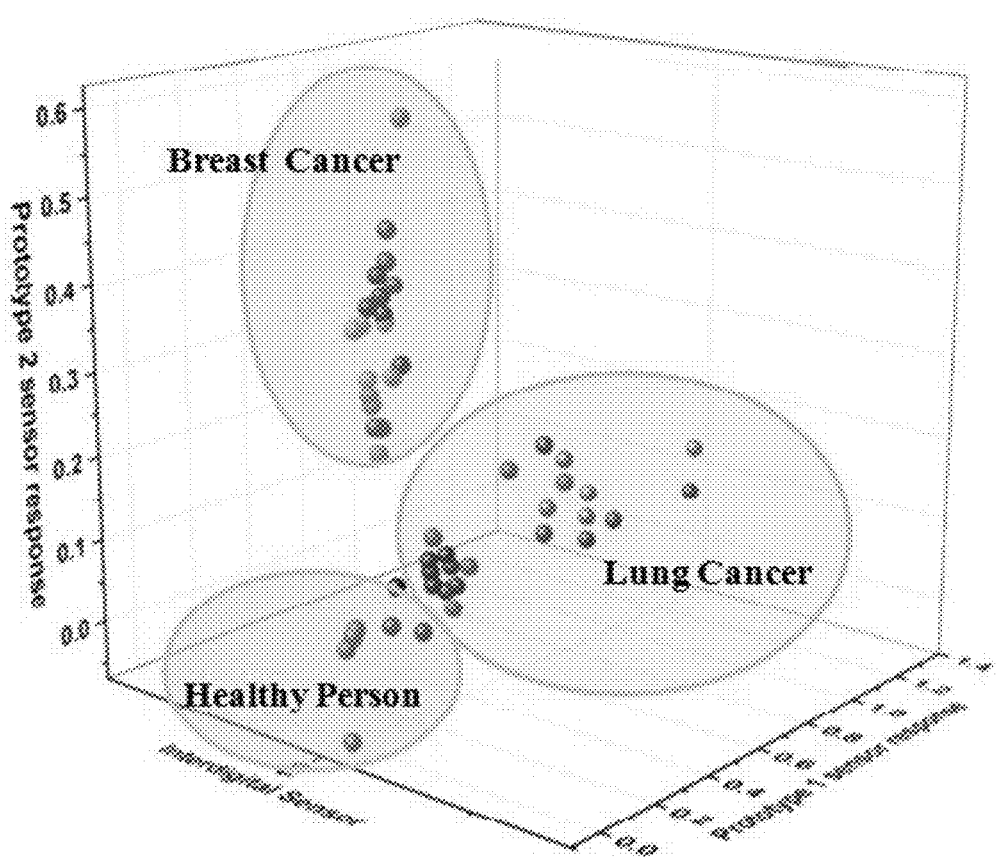
FIG. 8 depicts an example of a user interface output by a diagnostic module, according to one embodiment of the disclosure.

FIG. 7 and FIG. 8 provide example user interface outputs by a diagnostic module. In some embodiments, biomarkers are also useful for diagnosis, monitoring disease progression, and predicting diseases recurrence. For example, a cancer biomarker, which refers to a substance or process that is indicative of the presence of cancer in the body, can be monitored using the devices described herein.

Many modifications and other embodiments of the example descriptions set forth herein to which these descriptions pertain will come to mind having the benefit of the teachings presented in the foregoing descriptions and the associated drawings. Thus, it will be appreciated that the disclosure may be embodied in many forms and should not be limited to the example embodiments described above.

Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

The claimed subject matter is:

1. A system for detecting and identifying one or more volatile organic compounds (VOCs) associated with coronavirus disease 2019 in exhaled breath of a subject, the system comprising:
   a mouth piece connected to a housing, the mouth piece operable to receive the exhaled breath of the subject;
   a sensor module disposed in the housing,
      the sensor module operable to detect the one or more VOCs associated with coronavirus disease 2019 in the exhaled breath, and further operable to collect data associated with detection of the one or more VOCs,
      wherein the sensor module comprises at least one sensor component operable to detect the one or more VOCs, wherein the sensor component comprises one or more sensors embedded with a composite of graphite or nanomaterial allotropes of carbon and a polymer matrix with non-polar long chain hydrocarbon, one or more sensors embedded with a composite of graphite or nanomaterial allotropes of carbon and a polymer matrix with polar hydrazine derivative and polystyrene, and one or more sensors embedded with a composite of graphite or nanomaterial allotropes of carbon and a polymer matrix with dicyclohexyl urea and polystyrene; and
   a communication module disposed in the housing and in communication with the sensor module, wherein the communication module is operable to transmit collected data from the sensor module to a mobile communication device associated with the subject.

2. The system of claim 1, wherein the VOCs comprise one or more of ketone, acetone, an aldehyde, an acetaldehyde, a hydrocarbon, an alkane, a pentane, an alkene, and a fatty acid.

3. The system of claim 1, wherein the VOCs comprise alkanes aldehydes, and carbonyl compounds.

4. The system of claim 1, further comprising:
   a biomarker processing module, in communication with the sensor module, and operable to process the collected data associated with detection of the one or more VOCs and to identify the one or more VOCs, wherein the detection of the one or more VOCs occurs in less than one minute.

5. The system of claim 4, wherein the biomarker processing module is further operable to process the collected data via a neural network or pattern recognition algorithm, wherein a result from the biomarker processing module is received by the communication module for output to the mobile communication device associated with the subject.

6. The system of claim 4, wherein the biomarker processing module is further operable to process the collected data in conjunction with other sensor data, wherein a result from the biomarker processing module is received by the communication module for output to the mobile communication device associated with the subject.

7. The system of claim 1, wherein the sensor component comprises
   an activity sensor operable to detect or measure one or more physical actions by the subject, and further operable to collect data associated with detection or measurement of the one or more physical actions; and
   wherein the communication module is in communication with the activity sensor, and the communication module is further operable to transmit collected data from the activity sensor to the mobile communication device associated with the subject.

8. The system of claim 1, wherein the communication module is further operable to transmit collected data via at least one of the following: infrared (IR) communication, wireless communication, a Bluetooth protocol wireless communication, a direct wired connection, or to a remote memory storage device.

9. The system of claim 1, wherein the system is a handheld device.

10. The system of claim 1, wherein the sensor component comprises at least one interdigitated electrode and/or at least one fractal electrode.

11. The system of claim 1, wherein the sensor component comprises sixteen interdigitated electrodes and/or fractal electrodes.

* * * * *